(12) United States Patent
Brys et al.

(10) Patent No.: US 9,945,843 B2
(45) Date of Patent: Apr. 17, 2018

(54) METHODS FOR IDENTIFYING COMPOUNDS THAT INHIBIT G PROTEIN-COUPLED RECEPTOR (GPR84) AGONIST-STIMULATED CHEMOTAXIS

(71) Applicant: GALAPAGOS NV, Mechelen (BE)

(72) Inventors: Reginald Christophe Xavier Brys, Mechelen (BE); Sonia Dupont, Romainville (FR)

(73) Assignee: GALAPAGOS NV, Mechelen (BE)

(*) Notice: Subject to any disclaimer, the term of this patent is extended or adjusted under 35 U.S.C. 154(b) by 239 days.

(21) Appl. No.: 14/367,565

(22) PCT Filed: Dec. 20, 2012

(86) PCT No.: PCT/EP2012/076277
§ 371 (c)(1),
(2) Date: Jun. 20, 2014

(87) PCT Pub. No.: WO2013/092793
PCT Pub. Date: Jun. 27, 2013

(65) Prior Publication Data
US 2015/0330968 A1    Nov. 19, 2015

(30) Foreign Application Priority Data
Dec. 22, 2011    (GB) .................................. 1122146.2

(51) Int. Cl.
*G01N 33/50* (2006.01)
*A61K 49/00* (2006.01)

(52) U.S. Cl.
CPC ..... *G01N 33/5029* (2013.01); *A61K 49/0008* (2013.01); *G01N 2333/726* (2013.01)

(58) Field of Classification Search
CPC ......... G01N 33/5029; G01N 2333/726; A61K 49/0008
See application file for complete search history.

(56) References Cited

U.S. PATENT DOCUMENTS

| | | | | |
|---|---|---|---|---|
| 8,691,498 B2 * | 4/2014 | Hakak | ......... | C07K 14/723 435/4 |
| 2010/0028929 A1 * | 2/2010 | Gravina | ......... | C07K 14/705 435/29 |

FOREIGN PATENT DOCUMENTS

| | | |
|---|---|---|
| WO | 2005050225 A2 | 6/2005 |
| WO | 2007027661 A2 | 3/2007 |

OTHER PUBLICATIONS

Lattin et al., 2007, "G-Protein-Coupled Receptor Expression, Function, and Signaling in Macrophages," Journal of Leukocyte Biology, 82:16-32.*
Russell et al., (2004) "IL-12 p40 Homodimer-Dependent Macrophage Chemotaxis and Respiratory Viral Inflammation are Mediated Through IL-12 Receptor .beta.1," Journal of Immunology, 171: 6866-74.*
Allavena et al., "Interleukin-12 is chemotactic for natural killer cells and stimulates their interaction with vascular endothelium." Blood, 84(7): 2261-2268, 1994.*
Wang, J et al; "Medium-chain fatty acids as ligands for orphan G protein-coupled receptor GPR84," Journal of Biological Chemistry, American Society for Biochemistry and Molecular Biology, US, vol. 281, No. 45, Sep. 11, 2006, pp. 34457-34464
Yousefi S et al; "Cloning and Expression Analysis of a Novel G-Protein-Coupled Receptor Selectively Expressed on Granulocytes," Journal of Leukocyte Biology, Federation of American Societies for Experimental Biology, US, vol. 69, No. 6, Jun. 1, 2001, pp. 1045-1052.
Hiroshi Nagasaki et al.; "Inflammatory changes in adipose tissue enhance expression of GPR84, a medium-chain fatty acid receptor," FEBS Letters, Elsevier, Amsterdam, NL, vol. 586, No. 4, Jan. 1, 2012, pp. 368-372.
International search report for PCT/EP2012/076277 dated Apr. 22, 2013.

* cited by examiner

*Primary Examiner* — Robert S Landsman
(74) *Attorney, Agent, or Firm* — Heslin Rothenberg Farley and Mesiti, PC

(57) ABSTRACT

The present invention relates to methods and assays for identifying agents capable of modulating GPR84 activity in cells, in particular agents that inhibit GPR84-agonist stimulated chemotaxis. Inhibition of GPR84-agonist stimulated chemotaxis is useful in the prevention and/or treatment of inflammatory conditions. In particular, the present invention provides methods and assays for identifying agents for use in the prevention and/or treatment of inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF)), neuroinflammatory conditions, infectious diseases, autoimmune diseases and/or diseases involving impairment of immune cell functions.

15 Claims, 3 Drawing Sheets

FIG. 1

```
Met Trp Asn Ser Ser Asp Ala Asn Phe Ser Cys Tyr His Glu Ser Val
1               5               10                  15

Leu Gly Tyr Arg Tyr Val Ala Val Ser Trp Gly Val Val Val Ala Val
            20              25              30

Thr Gly Thr Val Gly Asn Val Leu Thr Leu Leu Ala Leu Ala Ile Gln
            35              40              45

Pro Lys Leu Arg Thr Arg Phe Asn Leu Leu Ile Ala Asn Leu Thr Leu
    50              55              60

Ala Asp Leu Leu Tyr Cys Thr Leu Leu Gln Pro Phe Ser Val Asp Thr
65              70              75              80

Tyr Leu His Leu His Trp Arg Thr Gly Ala Thr Phe Cys Arg Val Phe
            85              90              95

Gly Leu Leu Leu Phe Ala Ser Asn Ser Val Ser Ile Leu Thr Leu Cys
            100             105             110

Leu Ile Ala Leu Gly Arg Tyr Leu Leu Ile Ala His Pro Lys Leu Phe
        115             120             125

Pro Gln Val Phe Ser Ala Lys Gly Ile Val Leu Ala Leu Val Ser Thr
    130             135             140

Trp Val Val Gly Val Ala Ser Phe Ala Pro Leu Trp Pro Ile Tyr Ile
145             150             155             160

Leu Val Pro Val Val Cys Thr Cys Ser Phe Asp Arg Ile Arg Gly Arg
            165             170             175

Pro Tyr Thr Thr Ile Leu Met Gly Ile Tyr Phe Val Leu Gly Leu Ser
        180             185             190

Ser Val Gly Ile Phe Tyr Cys Leu Ile His Arg Gln Val Lys Arg Ala
        195             200             205

Ala Gln Ala Leu Asp Gln Tyr Lys Leu Arg Gln Ala Ser Ile His Ser
    210             215             220

Asn His Val Ala Arg Thr Asp Glu Ala Met Pro Gly Arg Phe Gln Glu
225             230             235             240

Leu Asp Ser Arg Leu Ala Ser Gly Gly Pro Ser Glu Gly Ile Ser Ser
            245             250             255
```

FIG. 1 Cont'd.

Glu Pro Val Ser Ala Ala Thr Thr Gln Thr Leu Glu Gly Asp Ser Ser
            260                 265                 270

Glu Val Gly Asp Gln Ile Asn Ser Lys Arg Ala Lys Gln Met Ala Glu
        275                 280                 285

Lys Ser Pro Pro Glu Ala Ser Ala Lys Ala Gln Pro Ile Lys Gly Ala
    290                 295                 300

Arg Arg Ala Pro Asp Ser Ser Ser Glu Phe Gly Lys Val Thr Arg Met
305                 310                 315                 320

Cys Phe Ala Val Phe Leu Cys Phe Ala Leu Ser Tyr Ile Pro Phe Leu
            325                 330                 335

Leu Leu Asn Ile Leu Asp Ala Arg Val Gln Ala Pro Arg Val Val His
            340                 345                 350

Met Leu Ala Ala Asn Leu Thr Trp Leu Asn Gly Cys Ile Asn Pro Val
        355                 360                 365

Leu Tyr Ala Ala Met Asn Arg Gln Phe Arg Gln Ala Tyr Gly Ser Ile
    370                 375                 380

Leu Lys Arg Gly Pro Arg Ser Phe His Arg Leu His
385                 390                 395

SEQUENCE LISTING

```
<160> NUMBER OF SEQ ID NOS: 16

<210> SEQ ID NO 1
<211> LENGTH: 396
<212> TYPE: PRT
<213> ORGANISM: Homo sapiens

<400> SEQUENCE: 1

Met Trp Asn Ser Ser Asp Ala Asn Phe Ser Cys Tyr His Glu Ser Val
1               5                   10                  15

Leu Gly Tyr Arg Tyr Val Ala Val Ser Trp Gly Val Val Val Ala Val
            20                  25                  30

Thr Gly Thr Val Gly Asn Val Leu Thr Leu Leu Ala Leu Ala Ile Gln
        35                  40                  45

Pro Lys Leu Arg Thr Arg Phe Asn Leu Leu Ile Ala Asn Leu Thr Leu
    50                  55                  60

Ala Asp Leu Leu Tyr Cys Thr Leu Leu Gln Pro Phe Ser Val Asp Thr
65                  70                  75                  80

Tyr Leu His Leu His Trp Arg Thr Gly Ala Thr Phe Cys Arg Val Phe
                85                  90                  95

Gly Leu Leu Phe Ala Ser Asn Ser Val Ser Ile Leu Thr Leu Cys
            100                 105                 110

Leu Ile Ala Leu Gly Arg Tyr Leu Leu Ile Ala His Pro Lys Leu Phe
        115                 120                 125

Pro Gln Val Phe Ser Ala Lys Gly Ile Val Leu Ala Leu Val Ser Thr
    130                 135                 140

Trp Val Gly Val Ala Ser Phe Ala Pro Leu Trp Pro Ile Tyr Ile
145                 150                 155                 160

Leu Val Pro Val Cys Thr Cys Ser Phe Asp Arg Ile Arg Gly Arg
                165                 170                 175

Pro Tyr Thr Thr Ile Leu Met Gly Ile Tyr Phe Val Leu Gly Leu Ser
            180                 185                 190

Ser Val Gly Ile Phe Tyr Cys Leu Ile His Arg Gln Val Lys Arg Ala
        195                 200                 205

Ala Gln Ala Leu Asp Gln Tyr Lys Leu Arg Gln Ala Ser Ile His Ser
    210                 215                 220

Asn His Val Ala Arg Thr Asp Glu Ala Met Pro Gly Arg Phe Gln Glu
```

```
                225                 230                 235                 240

Leu Asp Ser Arg Leu Ala Ser Gly Gly Pro Ser Glu Gly Ile Ser Ser
                        245                 250                 255

Glu Pro Val Ser Ala Ala Thr Thr Gln Thr Leu Glu Gly Asp Ser Ser
                    260                 265                 270

Glu Val Gly Asp Gln Ile Asn Ser Lys Arg Ala Lys Gln Met Ala Glu
                    275                 280                 285

Lys Ser Pro Pro Glu Ala Ser Ala Lys Ala Gln Pro Ile Lys Gly Ala
                    290                 295                 300

Arg Arg Ala Pro Asp Ser Ser Glu Phe Gly Lys Val Thr Arg Met
        305                 310                 315                 320

Cys Phe Ala Val Phe Leu Cys Phe Ala Leu Ser Tyr Ile Pro Phe Leu
                        325                 330                 335

Leu Leu Asn Ile Leu Asp Ala Arg Val Gln Ala Pro Arg Val Val His
                        340                 345                 350

Met Leu Ala Ala Asn Leu Thr Trp Leu Asn Gly Cys Ile Asn Pro Val
                        355                 360                 365

Leu Tyr Ala Ala Met Asn Arg Gln Phe Arg Gln Ala Tyr Gly Ser Ile
                        370                 375                 380

Leu Lys Arg Gly Pro Arg Ser Phe His Arg Leu His
        385                 390                 395

<210> SEQ ID NO 2
<211> LENGTH: 26
<212> TYPE: PRT
<213> ORGANISM: Homo sapiens

<400> SEQUENCE: 2

Met Trp Asn Ser Ser Asp Ala Asn Phe Ser Cys Tyr His Glu Ser Val
1               5                   10                  15

Leu Gly Tyr Arg Tyr Val Ala Val Ser Trp
            20                  25

<210> SEQ ID NO 3
<211> LENGTH: 21
<212> TYPE: PRT
<213> ORGANISM: Homo sapiens

<400> SEQUENCE: 3

Gly Val Val Val Ala Val Thr Gly Thr Val Gly Asn Val Leu Thr Leu
1               5                   10                  15

Leu Ala Leu Ala Ile
            20

<210> SEQ ID NO 4
<211> LENGTH: 10
<212> TYPE: PRT
<213> ORGANISM: Homo sapiens

<400> SEQUENCE: 4

Gln Pro Lys Leu Arg Thr Arg Phe Asn Leu
1               5                   10

<210> SEQ ID NO 5
<211> LENGTH: 21
<212> TYPE: PRT
<213> ORGANISM: Homo sapiens

<400> SEQUENCE: 5
```

```
Leu Ile Ala Asn Leu Thr Leu Ala Asp Leu Leu Tyr Cys Thr Leu Leu
1               5                   10                  15

Gln Pro Phe Ser Val
            20

<210> SEQ ID NO 6
<211> LENGTH: 16
<212> TYPE: PRT
<213> ORGANISM: Homo sapiens

<400> SEQUENCE: 6

Asp Thr Tyr Leu His Leu His Trp Arg Thr Gly Ala Thr Phe Cys Arg
1               5                   10                  15

<210> SEQ ID NO 7
<211> LENGTH: 21
<212> TYPE: PRT
<213> ORGANISM: Homo sapiens

<400> SEQUENCE: 7

Val Phe Gly Leu Leu Leu Phe Ala Ser Asn Ser Val Ser Ile Leu Thr
1               5                   10                  15

Leu Cys Leu Ile Ala
            20

<210> SEQ ID NO 8
<211> LENGTH: 29
<212> TYPE: PRT
<213> ORGANISM: Homo sapiens

<400> SEQUENCE: 8

Leu Gly Arg Tyr Leu Leu Ile Ala His Pro Lys Leu Phe Pro Gln Val
1               5                   10                  15

Phe Ser Ala Lys Gly Ile Val Leu Ala Leu Val Ser Thr
            20                  25

<210> SEQ ID NO 9
<211> LENGTH: 21
<212> TYPE: PRT
<213> ORGANISM: Homo sapiens

<400> SEQUENCE: 9

Trp Val Val Gly Val Ala Ser Phe Ala Pro Leu Trp Pro Ile Tyr Ile
1               5                   10                  15

Leu Val Pro Val Val
            20

<210> SEQ ID NO 10
<211> LENGTH: 15
<212> TYPE: PRT
<213> ORGANISM: Homo sapiens

<400> SEQUENCE: 10

Cys Thr Cys Ser Phe Asp Arg Ile Arg Gly Arg Pro Tyr Thr Thr
1               5                   10                  15

<210> SEQ ID NO 11
<211> LENGTH: 21
<212> TYPE: PRT
<213> ORGANISM: Homo sapiens

<400> SEQUENCE: 11

Ile Leu Met Gly Ile Tyr Phe Val Leu Gly Leu Ser Ser Val Gly Ile
```

```
1               5                   10                  15

Phe Tyr Cys Leu Ile
            20

<210> SEQ ID NO 12
<211> LENGTH: 119
<212> TYPE: PRT
<213> ORGANISM: Homo sapiens

<400> SEQUENCE: 12

His Arg Gln Val Lys Arg Ala Ala Gln Ala Leu Asp Gln Tyr Lys Leu
1               5                   10                  15

Arg Gln Ala Ser Ile His Ser Asn His Val Ala Arg Thr Asp Glu Ala
            20                  25                  30

Met Pro Gly Arg Phe Gln Glu Leu Asp Ser Arg Leu Ala Ser Gly Gly
        35                  40                  45

Pro Ser Glu Gly Ile Ser Ser Glu Pro Val Ser Ala Ala Thr Thr Gln
    50                  55                  60

Thr Leu Glu Gly Asp Ser Ser Glu Val Gly Asp Gln Ile Asn Ser Lys
65                  70                  75                  80

Arg Ala Lys Gln Met Ala Glu Lys Ser Pro Pro Glu Ala Ser Ala Lys
                85                  90                  95

Ala Gln Pro Ile Lys Gly Ala Arg Arg Ala Pro Asp Ser Ser Ser Glu
            100                 105                 110

Phe Gly Lys Val Thr Arg Met
        115

<210> SEQ ID NO 13
<211> LENGTH: 21
<212> TYPE: PRT
<213> ORGANISM: Homo sapiens

<400> SEQUENCE: 13

Cys Phe Ala Val Phe Leu Cys Phe Ala Leu Ser Tyr Ile Pro Phe Leu
1               5                   10                  15

Leu Leu Asn Ile Leu
            20

<210> SEQ ID NO 14
<211> LENGTH: 11
<212> TYPE: PRT
<213> ORGANISM: Homo sapiens

<400> SEQUENCE: 14

Asp Ala Arg Val Gln Ala Pro Arg Val Val His
1               5                   10

<210> SEQ ID NO 15
<211> LENGTH: 21
<212> TYPE: PRT
<213> ORGANISM: Homo sapiens

<400> SEQUENCE: 15

Met Leu Ala Ala Asn Leu Thr Trp Leu Asn Gly Cys Ile Asn Pro Val
1               5                   10                  15

Leu Tyr Ala Ala Met
            20

<210> SEQ ID NO 16
<211> LENGTH: 23
```

```
<212> TYPE: PRT
<213> ORGANISM: Homo sapiens

<400> SEQUENCE: 16

Asn Arg Gln Phe Arg Gln Ala Tyr Gly Ser Ile Leu Lys Arg Gly Pro
1               5                   10                  15

Arg Ser Phe His Arg Leu His
            20
```

METHODS FOR IDENTIFYING COMPOUNDS THAT INHIBIT G PROTEIN-COUPLED RECEPTOR (GPR84) AGONIST-STIMULATED CHEMOTAXIS

CROSS-REFERENCE TO RELATED APPLICATIONS

This application is a national stage filing under section 371 of International Application No. PCT/EP2012/076277, filed on Dec. 20, 2012, and published on Jun. 27, 2013 as WO 2013/092793 A1, and claims priority to Great Britain Patent Application No. GB1122146.2 filed on Dec. 22, 2011. The entire disclosures of each of the prior applications are hereby incorporated herein by reference.

SEQUENCE LISTING

This application contains a Sequence Listing; the file, in ASCII format, is designated 3622005_SeqList_ST25.txt and is 8.6 kilobytes in size. The sequence listing file is hereby incorporated by reference in its entirety into the application.

FIELD OF THE INVENTION

The present invention provides evidence that GPR84 agonists induce neutrophil chemotaxis and that GPR84 antagonists may be able to block GPR84 agonist-stimulated chemotaxis. These results indicate that GPR84 is an essential player in the process of neutrophil recruitment. The present invention therefore relates to a novel assay for the identification of compounds that inhibit GPR84-agonist stimulated chemotaxis, a process that is involved in inflammatory conditions. In a particular the inflammatory conditions are selected from inflammatory bowel disorder (IBD), rheumatoid arthritis, chronic obstructive pulmonary disease (COPD), and idiopathic pulmonary fibrosis (IPF).

The present invention also provides methods for the identification of compounds useful in the prevention and/or treatment of inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF)), neuroinflammatory conditions, infectious diseases, autoimmune diseases and/or diseases involving impairment of immune cell functions.

BACKGROUND OF THE INVENTION

GPR84 was recently isolated and characterized from human B cells (Wittenberger et al., 2001, J Mol Biol, 307, 799-813) as the result of an expressed sequence tag data mining strategy, and also using a degenerate primer reverse transcriptase-polymerase chain reaction (RT-PCR) approach aimed to identify novel chemokine receptors expressed in neutrophils (Yousefi 2001).

GPR84 (also known as EX33) remained an orphan GPCR until the identification of medium-chain fatty acids (MCFA) with carbon chain lengths of 9-14 as ligands for this receptor (Wang 2006). GPR84 was described to be activated by capric acid, undecanoic acid and lauric acid with potencies of 5 µM, 9 µM and 11 µM, respectively. Two small molecules were also described to have some GPR84 agonist activity: 3,3'di indolylmethane (DIM) (Wang 2006) and Embelin (WO 2007/027661).

GPR84 expression has been shown to be expressed in immune cells including, but not limited to, polymorphonuclear leukocytes (PMN), neutrophils, monocytes, T cells, and B cells. (Wang 2006, Yousefi 2001, Venkataraman 2005, WO2007/027661). Higher levels of GPR84 were measured in neutrophils and eosinophils than in T-cells and B-cells. GPR84 expression was demonstrated in tissues that may play a role in the propagation of the inflammatory response such as lung, spleen, bone marrow.

For example, in a recent review, Du Bois reported the current status of therapies for lung interstitial diseases, such as idiopathic pulmonary fibrosis (IPF). There are almost 300 distinct injurious or inflammatory causes of interstitial lung disease that can result in diffuse lung scarring, and the initial stages of the IPF pathology are very likely to involve inflammation (Du Bois 2010), and combination therapies involving anti-inflammatory treatment could be advantageously used.

The expression of GPR84 was highly up-regulated in monocytes/macrophages upon LPS stimulation (Wang 2006).

GPR84 knock-out (KO) mice are viable and indistinguishable from wild-type littermate controls (Venkataraman 2005). The proliferation of T and B cells in response to various mitogens is reported to be normal in GPR84-deficient mice (Venkataraman 2005). T helper 2 (Th2) differentiated T cells from GPR84 KO secreted higher levels of IL4, IL5, IL13, the 3 major Th2 cytokines, compared to wild-type littermate controls. In contrast, the production of the Th1 cytokine, INFγ, was similar in Th1 differentiated T cells from GPR84 KO and wild-type littermate (Venkataraman 2005).

In addition, Capric acid, undecanoic acid and lauric acid dose-dependently increased the secretion of interleukin-12 p40 subunit (IL-12 p40) from RAW264.7 murine macrophage-like cells stimulated with LPS. The pro-inflammatory cytokine IL-12 plays a pivotal role in promoting cell-mediated immunity to eradicate pathogens by inducing and maintaining T helper 1 (Th1) responses and inhibiting T helper 2 (Th2) responses. MCFAs, through their direct actions on GPR84, may affect Th1/Th2 balance.

Berry et al. identified a whole-blood 393-gene transcriptional signature for active tuberculosis (TB) (Berry 2010). GPR84 was part of this whole-blood 393-gene transcriptional signature for active TB indicating a potential role for GPR84 in infectious diseases.

GPR84 expression was also described in the microglia, primary immune effector cells of the central nervous system (CNS) from myeloid-monocytic origin (Bouchard 2007). As observed in peripheral immune cells, GPR84 expression in microglia was highly inducible under inflammatory conditions such as TNFα and IL1 treatment but also notably endotoxemia and experimental autoimmune encephalomyelitis (EAE), suggesting a role in neuro-inflammatory processes. Those results suggest that GPR84 would be up-regulated in CNS not only during endotoxemia and multiple sclerosis, but also in all neurological conditions in which TNFα or IL1b pro-inflammatory cytokines are produced, including brain injury, infection, Alzheimer's disease (AD), Parkinson's disease (PD).

Neutrophil chemotaxis to sites of infection is crucial for the host's innate immune defense (Kubes 2002). Unregulated directional motility can lead to disorders such as chronic inflammation (Woolhouse 2002) and other disorders. Chemotaxis, migration directed by gradients of chemotactic agents, is a complex process that involves extracellular and intracellular signaling, regulation of the cytoskeleton, and interactions between cells and the extracellular matrix (Chung 2001). The migration of neutrophils is guided by a number of common chemotactic agents such as the bacterial product formyl-Met-Leu-Phe (fMLP) and host derived products like interleukin 8 (IL-8) and leukotriene B4 (LTB4) (Foxman 1997; Foxmann 1999; Baggiolini 1998).

Neutrophils sense the presence of chemotactic agents through the use of G-protein coupled receptors. This class of receptors is huge, representing a significant portion of the genome. The main classes of chemotaxis receptors are triggered by formyl peptides—formyl peptide receptors (FPR), chemokines—chemokine receptors (CCR or CXCR) and leukotrienes—leukotriene receptors (BLT).

It was suggested that GPR84 might be involved in the regulation of chemotaxis (Yousefi 2001). However, the authors proposed that GPR84 plays role in the classical chemotaxis pathway driven by IL8 and fMLP. As is demonstrated further herein and exemplified by the present invention, the role of GPR84 in neutrophil chemotaxis is highly specific and is not linked to the classical chemotaxis pathway, in fact GPR84 antagonists have no effect on the chemotaxis stimulated by the agents proposed in the publication by Yousefi.

The present invention provides evidence that GPR84 is involved in chemotaxis of immune cells, but not via one of the classic chemotaxis pathways described above. The present invention provides a novel assay for the identification of compounds that modulate GPR84 activity, in particular inhibit GPR84-agonist stimulated chemotaxis, and further a method for the identification of compounds useful in the prevention and/or treatment of inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF)), neuroinflammatory conditions, infectious diseases, autoimmune diseases and/or diseases involving impairment of immune cell functions.

SUMMARY OF THE INVENTION

The present invention is based on the discovery that compounds that inhibit the activity of GPR84 are able to inhibit the chemotaxis of immune cells such as neutrophils, macrophages and dendritic cells, in particular neutrophils. Said compounds are useful in the treatment of inflammatory conditions, neuro-inflammatory conditions, infectious diseases, autoimmune diseases and/or diseases involving impairment of immune cell functions, as can be demonstrated by the activity of said compounds in a variety of further cellular and in vivo models. In a particular embodiment the inflammatory conditions are selected from inflammatory bowel disorder (IBD), rheumatoid arthritis, chronic obstructive pulmonary disease (COPD), and idiopathic pulmonary fibrosis (IPF).

The present invention provides a method for identifying a compound that inhibits GPR84-agonist stimulated chemotaxis, said method comprising: exposing a population of immune cells expressing GPR84 polypeptide comprising amino acid sequence SEQ ID NO: 1 to a test compound in the presence of a GPR84-agonist, and measuring a property related to the inhibition of chemotaxis of said immune cells.

Another aspect of this invention relates to the use of agents which inhibit GPR84 as disclosed herein in a therapeutic method, a pharmaceutical composition, and the manufacture of such composition, useful for the treatment of inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF)), neuroinflammatory conditions, infectious diseases, autoimmune diseases and/or diseases involving impairment of immune cell functions.

BRIEF DESCRIPTION OF THE DRAWINGS

FIG. 1. This figure shows the amino acid sequence of GPR84 (SEQ ID NO: 1)

DETAILED DESCRIPTION

Figure 2:
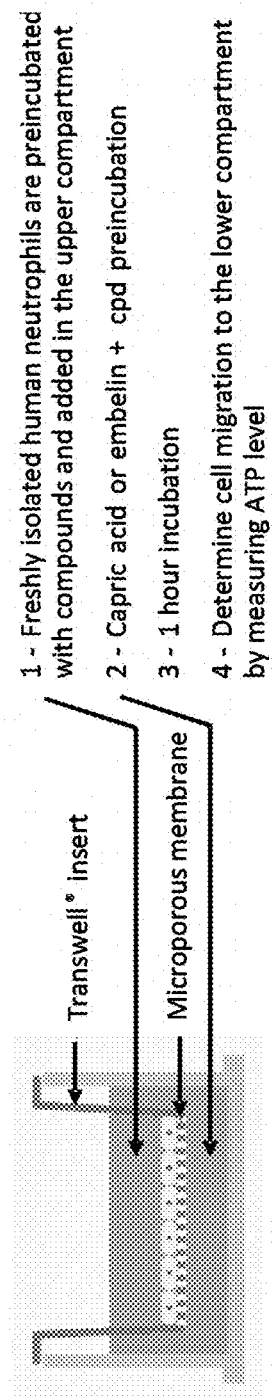
FIG. 2. This figure shows the neutrophil migration assay setup.

The following terms are intended to have the meanings presented therewith below and are useful in understanding the description and intended scope of the present invention.

The term 'GPR84 agonist' or 'agonist of GPR84' as used herein refers to any agent that stimulates GPR84 in the broadest sense. Particular examples of such agents include capric acid, undecanoic acid, lauric acid, 2,5-dihydroxy-3-undecyl-2,5-cyclohexadiene-1,4-dione (Embelin), icosa-5,8,11,14-tetraynoic acid, 5S,6R-dihydroxy-icosa-7,9,11,14-tetraynoic acid, diindorylmethane and indol-3-carbinol.

The term 'compound' means any molecule, including polypeptides, polynucleotides, natural products and small molecules. In particular the term includes test compounds or drug candidate compounds. The compounds include inorganic or organic compounds such as polynucleotides (e.g. siRNA or cDNA), lipids or hormone analogs. Other biopolymeric organic test compounds include peptides comprising from about 2 to about 40 amino acids and larger polypeptides comprising from about 40 to about 500 amino acids, including polypeptide ligands, enzymes, receptors, channels, antibodies or antibody conjugates.

As used herein the term 'autoimmune disease(s)' refers to the group of diseases including obstructive airways disease (including conditions such as COPD (Chronic obstructive pulmonary disease)), psoriasis, asthma (e.g. intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, vasculitis, inflammatory bowel disease (e.g. Crohn's disease and ulcerative colitis), atherosclerosis and amyotrophic lateral sclerosis. Particularly the term refers to COPD, asthma, psoriasis, systemic lupus erythematosus, type I diabetes mellitus, vasculitis and inflammatory bowel disease.

The term 'activity inhibitory agent' or 'activity inhibiting agent' means an agent, e.g. a polypeptide, small molecule, compound designed to interfere or capable of interfering selectively with the activity or expression of a specific polypeptide or protein normally expressed within a cell.

The term 'agonist' refers to an agent that stimulates the receptor the agent binds to in the broadest sense.

As used herein, the term 'antagonist' is used to describe an agent that does not provoke a biological response itself upon binding to a receptor, but blocks or dampens agonist-mediated responses, or prevents or reduces agonist binding and, thereby, agonist-mediated responses.

The term 'assay' means any process used to measure a specific property of an agent, including a compound. A 'screening assay' means a process used to characterize or select compounds based upon their activity from a collection of compounds.

The term 'binding affinity' is a property that describes how strongly two or more compounds associate with each other in a non-covalent relationship. Binding affinities can be characterized qualitatively, (such as 'strong', 'weak', 'high', or low') or quantitatively (such as measuring the KD).

The term 'classical chemotactic agent' herein will refer to any agent known to induce chemotaxis of immune cells, in particular neutrophils. Such agents might act via different receptors, pathways and mechanisms. Examples of such well-known agents include, but are not limited to, IL8 (human), KC/CXCL1 (rat), N-formylmethionyl-leucyl-phenylalanine (fMLP), LTB4 and C5a.

The term 'complex' means the entity created when two or more compounds bind to, contact, or associate with each other.

The term 'compound' is used herein in the context of a 'test compound' or a 'drug candidate compound' described in connection with the assays of the present invention. As such, these compounds comprise organic or inorganic compounds, derived synthetically or from natural sources. The term 'condition' or 'disease' means the overt presentation of symptoms (i.e., illness) or the manifestation of abnormal clinical indicators (for example, biochemical indicators). Alternatively, the term 'disease' refers to a genetic or environmental risk of or propensity for developing such symptoms or abnormal clinical indicators.

The term 'contact' or 'contacting' means bringing at least two moieties together, whether in an in vitro system or an in vivo system.

The term 'derivatives of a polypeptide' relates to those peptides, oligopeptides, polypeptides, proteins and enzymes that comprise a stretch of contiguous amino acid residues of the polypeptide and that retain a biological activity of the protein, for example, polypeptides that have amino acid mutations compared to the amino acid sequence of a naturally-occurring form of the polypeptide. A derivative may further comprise additional naturally occurring, altered, glycosylated, acylated or non-naturally occurring amino acid residues compared to the amino acid sequence of a naturally occurring form of the polypeptide. It may also contain one or more non-amino acid substituents, or heterologous amino acid substituents, compared to the amino acid sequence of a naturally occurring form of the polypeptide, for example a reporter molecule or other ligand, covalently or non-covalently bound to the amino acid sequence.

As used herein, the term 'diseases involving impairment of immune cell functions' includes conditions with symptoms such as recurrent and drawn out viral and bacterial infections, and slow recovery. Other invisible symptoms may be the inability to kill off parasites, yeasts and bacterial pathogens in the intestines or throughout the body.

The term 'endogenous' shall mean a material that a mammal naturally produces. Endogenous in reference to the term G-Protein Coupled Receptor ('GPCR') shall mean that which is naturally produced by a mammal (for example, and not by limitation, a human). In contrast, the term non-endogenous in this context shall mean that which is not naturally produced by a mammal (for example, and not by limitation, a human). Both terms can be utilized to describe both in vivo and in vitro systems. For example, and without limitation, in a screening approach, the endogenous or non-endogenous GPR84 may be in reference to an in vitro screening system. As a further example and not limitation, where the genome of a mammal has been manipulated to include a non-endogenous polypeptide, screening of a candidate compound by means of an in vivo system is feasible. Endogenous may also refer to a ligand of GPR84 polypeptide. Such naturally occurring ligands might be present in the cell and be produced by a cell.

The term 'expressible nucleic acid' means a nucleic acid coding for or capable of encoding a proteinaceous molecule, peptide or polypeptide, and may include an RNA molecule, or a DNA molecule.

The term 'expression' comprises both endogenous expression and non-endogenous expression, including overexpression by transduction or transfection.

The term 'fragment of a polypeptide' relates to peptides, oligopeptides, polypeptides, proteins, monomers, subunits and enzymes that comprise a stretch of contiguous amino acid residues, and exhibit substantially a similar, but not necessarily identical, functional or expression activity as the complete sequence. In a particular aspect, 'fragment' may refer to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of said complete sequence.

The term "immune cell" refers to any cell actively involved in immune responses, including progenitors of such cells. The origin of such cells is not limited to human, but to any mammalian organism. Examples of immune cells include neutrophils, macrophages and dendritic cells.

As used herein the term "inflammatory condition(s)" refers to the group of conditions including, rheumatoid arthritis, osteoarthritis, juvenile idiopathic arthritis, vasculitis, psoriasis, gout, allergic airway disease (e.g. asthma, rhinitis), inflammatory bowel diseases (e.g. Crohn's disease, ulcerative colitis), and endotoxin-driven disease states (e.g. complications after bypass surgery or chronic endotoxin states contributing to e.g. chronic cardiac failure). Particularly the term refers to rheumatoid arthritis, allergic airway disease (e.g. asthma) and inflammatory bowel diseases.

As used herein, the term "infectious diseases" refers to bacterial infectious diseases and includes but is not limited to conditions such as sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, or enterobacteria species.

The term 'inhibit' or 'inhibiting', in relationship to the term 'response' means that a response is decreased or prevented in the presence of a compound as opposed to in the absence of the compound.

The term 'inhibition' refers to the reduction, down regulation of a process or the elimination of a stimulus for a process, which results in the absence or minimization of the expression or activity of a protein or polypeptide.

The term 'induction' refers to the inducing, up-regulation, or stimulation of a process, which results in the expression, enhanced expression, activity, or increased activity of a protein or polypeptide.

The term ligand' means an endogenous, naturally occurring molecule specific for an endogenous, naturally occurring receptor.

The term "mammalian cells" means cells derived from mammalian species. Preferred cells are human cells. Mammalian cells include feline, canine, bovine, equine, caprine, ovine, porcine, murine, such as mice and rats, and rabbits.

As used herein the term "neuroinflammatory conditions" refers to diseases or disorders characterized by abrupt neurologic deficits associated with inflammation, demyelination, and axonal damage, and includes but is not limited to conditions such as Guillain-Barré syndrome (GBS), multiple sclerosis, axonal degeneration, and autoimmune encephalomyelitis.

The term 'polypeptide' relates to proteins (such as GPR84), proteinaceous molecules, fragments of proteins, monomers or portions of polymeric proteins, peptides, oligopeptides and enzymes (such as kinases, proteases, GPCR's etc.).

The term 'polynucleotide' means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more particularly 70 percent of its base pairs are in common, particularly 80 percent, most particularly 90 percent, and in a special embodiment 100 percent of its base pairs. The polynucleotides include polyribonucleic acids, polydeoxyribonucleic acids, and synthetic analogues thereof. It also includes nucleic acids with modified backbones such as peptide nucleic acid (PNA), polysiloxane, and 2'-O-(2-methoxy)ethylphosphorothioate. Another special embodiment are nucleic acids with modified backbones such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection. Polynucleotides herein are selected to be 'substantially' complementary to different strands of a particular target DNA sequence. This means that the polynucleotides must be sufficiently complementary to hybridize with their respective strands. Therefore, the polynucleotide sequence need not reflect the exact sequence of the target sequence. For example, a non-complementary nucleotide fragment may be attached to the 5' end of the polynucleotide, with the remainder of the polynucleotide sequence being complementary to the strand. Alternatively, non-complementary bases or longer sequences can be interspersed into the polynucleotide, provided that the polynucleotide sequence has sufficient complementarity with the sequence of the strand to hybridize therewith under stringent conditions or to form the template for the synthesis of an extension product.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'system suitable for measuring chemotaxis' shall be understood as any assay or assembly suitable for measuring cell migration and in particular cell chemotaxis. Examples of such assays are provided herein, but those examples should not be considered limiting. Any suitable chemotaxis measurement assay can be used.

The term 'subject' includes humans and other mammals.

'The term 'treating' means an intervention performed with the intention of preventing the development or altering the pathology of, and thereby ameliorating a disorder, disease or condition, including one or more symptoms of such disorder or condition. Accordingly, 'treating' refers to both therapeutic treatment and prophylactic or preventative measures. Those in need of treating include those already with the disorder as well as those in which the disorder is to be prevented. The related term 'treatment,' as used herein, refers to the act of treating a disorder, symptom, disease or condition, as the term 'treating' is defined above.

The term 'treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter or of a physiologically measurable parameter), or both. In a further embodiment, 'treating' or 'treatment' relates to slowing the progression of the disease.

GPR84

The present invention demonstrates that GPR84 agonists (for example medium-chain fatty acids) induce neutrophil chemotaxis and that GPR84 antagonists are able to specifically block this chemotaxis, indicating that G Protein-Coupled Receptor 84 (GPR84) is an essential player in the process of neutrophil recruitment. The migration of neutrophils is typically guided by a number of common chemotactic agents such as bacterial product formyl-Met-Leu-Phe (fMLP) and host derived products like interleukin 8 (IL-8) and leukotriene B4 (LTB4) (Foxman 1997; Foxmann 1999; Baggiolini 1998). Neutrophils sense the presence of chemotactic agents through the use of different G-protein coupled receptors. The main classes of chemotaxis receptors are triggered by formyl peptides—formyl peptide receptors (FPR), chemokines—chemokine receptors (CCR or CXCR) and leukotrienes—leukotriene receptors (BLT). The experiments using the typical chemotactic agents like IL8, neutrophil-activating factor-78, formyl-Met-Leu-Phe (fMLP) revealed that these are not ligands for GPR84 (Yosefi 2001). GPR84 is activated by other classes of agonists, exemplary GPR84 agonists include sodium decanoate, 3,3' di indolylmethane and 2,5-dihydroxy-3-undecyl-2,5-cyclohexadiene-1,4-dione (Embelin). Particularly, the present invention demonstrates that GPR84 antagonists do not block the chemotaxis stimulated by classical chemotactic agents, including that stimulated by IL8. This demonstrates that the GPR84 acts via a separate and distinct chemotaxic pathway and that the agonists of GPR84 have an individual role to play in neutrophil recruitment.

GPR84 is a GPCR and as is typical for its class, contains seven transmembrane domains linking extracellular and intracellular domains. The GPR84 polypeptide has length of 396 amino acids (FIG. 1) and the predicted locations of the transmembrane, intracellular and extracelluar domains are listed in Table 1.

TABLE 1

Predicted sequence features for the GPR84 polypeptide (source: UniProt)

| AA POS | SEQ ID NO | Length | Domain | Sequence |
|---|---|---|---|---|
| 1-26 | 2 | 26 | Extracellular | MWNSSDANFSCYHESVLGYRYVAVSW |
| 27-47 | 3 | 21 | Transmembrane | GVVVAVTGTVGNVLTLLALAI |
| 48-57 | 4 | 10 | Intracellular | QPKLRTRFNL |
| 58-78 | 5 | 21 | Transmembrane | LIANLTLADLLYCTLLQPFSV |
| 79-94 | 6 | 16 | Extracellular | DTYLHLHWRTGATFCR |
| 95-115 | 7 | 21 | Transmembrane | VFGLLLFASNSVSILTLCLIA |
| 116-144 | 8 | 29 | Intracellular | LGRYLLIAHPKLFPQVFSAKGIVLALVST |
| 145-165 | 9 | 21 | Transmembrane | WVVGVASFAPLWPIYILVPVV |
| 166-180 | 10 | 15 | Extracellular | CTCSFDRIRGRPYTT |
| 181-201 | 11 | 21 | Transmembrane | ILMGIYFVLGLSSVGIFYCLI |
| 202-320 | 12 | 119 | Intracellular | HRQVKRAAQALDQYKLRQASIHSNHVARTDEAMPGRFQELDSRLASGGPSEGISSEPVSAATTQTLEGDSSEVGDQINSKRAKQMAEKSPPEASAKAQPIKGARRAPDSSSEFGKVTRM |
| 321-341 | 13 | 21 | Transmembrane | CFAVFLCFALSYIPFLLLNIL |
| 342-352 | 14 | 11 | Extracellular | DARVQAPRVVH |
| 353-373 | 15 | 21 | Transmembrane | MLAANLTWLNGCINPVLYAAM |
| 374-396 | 16 | 23 | Intracellular | NRQFRQAYGSILKRGPRSFHRLH |

The present invention provides a method for identifying a compound that inhibits GPR84-agonist stimulated chemotaxis, said method comprising:
 a. exposing a population of cells to a test compound in the presence of a GPR84 agonist in a system suitable for measuring chemotaxis; and
 b. measuring a property related to the inhibition of chemotaxis of said cells in said system.

In a particular embodiment said cell has been tested to establish that is expresses a GPR84 polypeptide. In a special embodiment such cell might be engineered to over-express a GPR84 polypeptide. The methods of over-expressing a peptide are well established and are known to a skilled artisan.

In a particular embodiment the assay method might be supplemented by additional measurements to further study the binding of the test compound to GPR84 polypeptide. The assay method in that case comprises the additional steps of:
 a. contacting a test compound with GPR84 polypeptide comprising amino acid sequence SEQ ID NO: 1 and/or fragments thereof comprising amino acid sequences selected from the group consisting of SEQ ID NOs 2, 6, 10, 12, and 14; and
 b. measuring a property related to the activity and/or expression of GPR84 polypeptide.

Suitable controls should always be in place to insure against false positive readings. In a particular embodiment of the present invention the screening method comprises the additional step of comparing the compound to a suitable control. In one embodiment, the control may be a cell that has not been in contact with the test compound but is only exposed to a GPR84 agonist. In another aspect of such an embodiment the test cell is naturally expressing the GPR84 polypeptide and the control cell may have been contacted with a known antagonist of GPR84 in the presence of a GPR84 agonist. Such antagonist might be a compound which inhibits or prevents expression of the GPR84. In another aspect of such an embodiment the control cell is an immune cell in the presence of a classical chemotactic agent, for example IL8 (human), KC/CXCL1 (rat), N-formylmethionyl-leucyl-phenylalanine (fMLP), LTB4 or C5a. In a more specific embodiment such chemotactic agent is IL8 or LTB4. Whilst exemplary controls are described herein, this should not be taken as limiting; it is within the scope of a person of skill in the art to select appropriate controls for the experimental conditions being used.

In order to perform the assay method a suitable GPR84 agonist must be used. In one embodiment of the invention the GPR84 agonist is selected from the group consisting of capric acid/sodium decanoate, undecanoic acid, lauric acid, Embelin, icosa-5,8,11,14-tetraynoic acid, 5S,6R-Dihydroxy-icosa-7,9,11,14-tetraynoic acid, diindorylmethane, and indol-3-carbinol. For each particular setup a specific chemotactic agent might be chosen depending on the exact assay setup and conditions. Embelin, icosa-5,8,11,14-tetraynoic acid and 5 S,6R-Dihydroxy-icosa-7,9,11,14-tetraynoic acid have been described as known GPR84 agonists in WO2007/027661. Diindorylmethane (DIM) and indol-3-carbinol have been described as GPR84 agonists (Takeda 2003). In a more specific embodiment Embelin or capric acid are used as a chemotactic agent.

In one aspect the chemotaxis of said immune cells is measured by counting the number of cells that have migrated into a second chamber, said counting may be performed directly or indirectly.

In order to evaluate the effect of a test compound on the chemotaxis of immune cells an appropriate property related to chemotaxis should be measured. Selection of a suitable property is dependent on the available equipment and the assay setup. In general, the most important requisite for the assay is to calibrate the incubation time of the assay both the immune cells and the test compound.

Too short incubation time results in no cells in the sample, while too long time perturbs the concentration gradients and measures more chemokinetic than chemotactic responses. One of the common techniques of measuring cell chemotaxis uses two-chamber approach. Chambers isolated by filters are proper tools for accurate determination of chemotactic behaviour. In particular such property is a cell count for the number of cells migrated from one compartment of the chamber to another. Different chambers might be used for evaluation of cell chemotaxis and those are well known to a skilled artisan and have been well described.

In a particular embodiment of the invention the number of migrated cells can be quantified using a transwell/modified Boyden chambers. The Boyden chamber, generally, consists of a cylindrical cell culture insert nested inside the well of a cell culture plate. The insert contains a membrane at the bottom with a defined pore size. Cells are seeded in the top of the insert in serum-free media, while a chemotactic agent is placed in the well below. The cells move through the pores toward the chemotactic agent below and can be stained or otherwise quantified in a plate reader.

In a particular embodiment the assay method utilizes Boyden chambers and the property related to chemotaxis is the number of migrated cells. The number of migrated cells may be determined using any method known to a person of skill in the art, but exemplary methods include measuring crystal violet staining with optical density determination at 495 nm, pre-incubating cells with calcein and quantifing the numbers of cells using absorbance 485/535, direct cell counting, turbidimetric measurement, measuring the levels of appropriate cell markers such neutrophil elastase, CD11, or peroxidase and radioactivity measurement of radioactive isotopes, for example $^{51}Cr$ by employing appropriately-labelled neutrophils.

In a particular embodiment of the invention the neutrophil migration in the assay method can be assessed using time-lapse video microscopy in a Zigmond chamber. In Zigmond chambers (Zigmond 1988), a drop of suspended cells is placed on the middle of the cover glass. After the cells have adhered, the ends of the cover glass are wiped dry, leaving a wet section with adhering cells. The cover glass prepared in this way is inverted onto the grooved microscope slide so that the cell-covered portion is centered over the bridge between the grooves. The clamps are installed, and cell-suspension media and chemotactic factor are pipetted into the two grooves until they are full and no bubbles remain. The chamber is then incubated. After a suitable period (depending on cell type and experiment goals) the slide is placed under a microscope and the orientation of cells is observed and quantified. The internal structures of the migrating cells can also be studied by using high-power light microscopy.

In particular embodiment the assay method can be performed using Dunn chemotaxis chamber with a microscopic readout. The Dunn Chemotaxis Chamber is described in detail in Zicha, 1991 and allows the behavior of cells subjected to a linear concentration gradient of chemotactic agent to be observed directly in the light microscope. The chamber was designed to have good optical properties and long-term stability of the gradient, thus permitting time-lapse recording of cell behaviour over many hours. The method of tracking cells in the recordings in order to obtain trajectories of cell locomotion will depend on the software available and a person of skill in the art will be able to select appropriate methods. Chemotaxis can be evaluated by assessing directional clustering of cell migration using standard methods for the statistical analysis of directional data (Zicha et 41997; Wells and Ridley, 2005).

The compounds identified using the method of the invention can be further tested in the presence of other chemotactic agents and known chemotaxis stimulants. In particular embodiment of the invention the compounds identified in assay method, are further selected if they do not affect IL8 or LTB4-stimulated chemotaxis of immune cells.

In a particular embodiment of the invention the assay method is performed as a cellular assay. The requirement for such cell is that they express and/or produce the relevant molecules or intermediate metabolites indicative of changes in the GPR84 activity. In particular such cells include dendritic cells, macrophages, and neutrophils. In a special embodiment such cells are neutrophils. Such cells can be derived from any mammals, but preferably from rodents and in particular from mouse and rat. In a more particular embodiment those cells are derived from a human subject.

In a special embodiment such cells are immune system cells derived from a human subject. In more specific embodiment said cellular assay is performed using are neutrophil cells, preferably from a human subject. The choice of source of such is however not considered crucial for the invention method to be successfully performed. Alternative any mammalian cells naturally expressing GPR84 and demonstrating chemotaxis function can be utilized.

The population of cells may be exposed to the compound or the mixture of compounds through different means, for instance by direct incubation in the medium.

Additional methods provided in the present invention can utilize different GPR84 activity measurements either based on GPR84 activity or expression, including cellular downstream mediators or activators, when performed in a cellular assay.

As a member of GPCR family, GPR84 is capable of activating an effector protein, resulting in changes in second messenger levels in the cell. The activity of GPR84 can be measured by measuring the activity level of such second messengers. One important and useful second messenger in the cell is cyclic AMP (cAMP). The activity levels can be measured by methods known to persons skilled in the art, either directly by ELISA or radioactive technologies or indirectly by reporter gene analysis. The activity level of the one or more secondary messengers may typically be determined with a reporter gene controlled by a promoter, wherein the promoter is responsive to the second messenger. Promoters known and used in the art for such purposes are the cyclic-AMP responsive promoter that is responsive for the cyclic-AMP levels in the cell. The reporter gene typically has a gene product that is easily detectable. The reporter gene can either be stably infected or transiently transfected in the host cell. Useful reporter genes are alkaline phosphatase, enhanced green fluorescent protein, destabilized green fluorescent protein, luciferase and β-galactosidase.

One particular means of measuring the activity or expression of the GPR84 polypeptide is to determine the amount of said polypeptide using a polypeptide binding agent, such as an antibody, or to determine the activity of said polypeptide in a biological or biochemical measure. A further means of measuring the activity or expression of the polypeptide is to determine the amount or extent of downstream biomarkers of GPR84 activity released by the cells treated with the test compound.

In one aspect of the invention the property related to the activity of GPR84 is the level of expression of GPR84 in the cell. GPR84 gene expression (mRNA levels) can be measured using techniques well-known to a skilled artisan. Particular examples of such techniques include northern analysis or real-time PCR. Those methods are indicative of the presence of nucleic acids encoding GPR84 in a sample, and thereby correlate with expression of the transcript from the polynucleotide.

Alternatively the expression levels of the signaling molecules can be measured using quantitative real time polymerase chain reaction (Q-PCR/qPCR/qrt-PCR). qPCR is a laboratory technique based on the PCR, which is used to amplify and simultaneously quantify a targeted DNA molecule. For one or more specific sequences in a DNA sample Real Time-PCR enables both detection and quantification. The quantity can be either an absolute number of copies or a relative amount when normalized to DNA input or additional normalizing genes.

Particular steps of the method involving contacting the GPR84 polypeptide with a test compound might be practiced in vitro, using one or more of the GPR84 protein, or fragments thereof, including monomers, peptides and oligopeptides.

In particular embodiment of the invention the test compounds are pre-selected from the group consisting of compounds of a screening library and compounds having binding affinity for a GPR84 polypeptide. Such compound libraries might be commercially available or generated in-house for a particular GPCR class of polypeptides.

In particular embodiment of the invention the assay method described above, including possible variations in the assay conditions, might be supplemented by additional measurement of binding affinity of the test compound to GPR84 polypeptide. In a special embodiment such method comprises the following additional steps:
 a. contacting said compound with GPR84 polypeptide comprising amino acid sequence SEQ ID NO: 1 and fragments thereof comprising amino acid sequence selected from the group consisting of SEQ ID NOs 2, 6, 10, 12, and 14;
 b. measuring the binding affinity of said compound to said GPR84 polypeptide or fragment thereof; and
 c. selecting a compound with a desired level of binding affinity to said polypeptide In more particular embodiment compounds with a binding affinity of at least 10 µM are further selected.

Both GPR84 polypeptide as well as the fragments exposed to the extracellular space might be utilized. Such fragments might be useful when testing antibodies against GPR84.

The binding affinity of a compound with the GPR84 polypeptide can be measured by methods known in the art, such as using surface plasmon resonance biosensors (Biacore®), by saturation binding analysis with a labeled compound (for example, Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as $IC_{50}$ or $EC_{50}$. The $IC_{50}$ represents the concentration of a compound that is required for 50% inhibition of activity of another ligand to the polypeptide. The $EC_{50}$ represents the concentration required for obtaining 50% of the maximum effect in any assay that measures TARGET function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, $IC_{50}$ and $EC_{50}$ values, for example, in the range of 100 nM to 1 pM; a moderate- to low-affinity binding relates to high Kd, $IC_{50}$ and $EC_{50}$ values, for example in the micromolar range.

GPR84 polypeptide useful in the practice of the present invention described herein may be free in solution, affixed to a solid support, borne on a cell surface, or located intracellularly. To perform the methods it is feasible to immobilize either the GPR84 polypeptide or the compound to facilitate separation of complexes from uncomplexed forms of the polypeptide, as well as to accommodate automation of the assay. Interaction (for example, binding of) of the GPR84 polypeptide with a compound can be accomplished in any vessel suitable for containing the reactants. Examples of such vessels include microtiter plates, test tubes, and microcentrifuge tubes. In one embodiment, a fusion protein can be provided which adds a domain that allows the polypeptide to be bound to a matrix. For example, the GPR84 polypeptide can be "His" tagged, and subsequently adsorbed onto Ni-NTA microtitre plates, or ProtA fusions with the GPR84 polypeptides can be adsorbed to IgG, which are then combined with the cell lysates (for example, (35)S-labelled) and the candidate compound, and the mixture incubated under conditions favorable for complex formation (for example, at physiological conditions for salt and pH). Following incubation, the plates are washed to remove any unbound label, and the matrix is immobilized. The amount of radioactivity can be determined directly, or in the supernatant after dissociation of the complexes. Alternatively, the complexes can be dissociated from the matrix, separated by SDS-PAGE, and the level of the protein binding to the GPR84 protein quantified from the gel using standard electrophoretic techniques.

Other techniques for immobilizing protein on matrices can also be used in the method of identifying compounds. Furthermore either the GPR84 or the compound can be immobilized utilizing conjugation of biotin and streptavidin. Biotinylated GPR84 protein molecules can be prepared from biotin-NHS (N-hydroxy-succinimide) using techniques well known in the art (for example, biotinylation kit, Pierce Chemicals, Rockford, Ill.), and immobilized in the wells of streptavidin-coated 96 well plates (Pierce Chemical). Alternatively, antibodies reactive with the GPR84 but which do not interfere with binding of the GPR84 to the compound can be derivatized to the wells of the plate, and the GPR84 can be trapped in the wells by antibody conjugation. As described above, preparations of a labeled candidate compound are incubated in the wells of the plate presenting the GPR84, and the amount of complex trapped in the well can be quantitated.

Depending on the choice of the skilled artisan, the present assay method may be designed to function as a series of measurements, each of which is designed to further confirm whether the drug candidate compound is acting on the GPR84 polypeptide to thereby modulate chemotaxis. For example, an assay designed to determine the binding affinity of a compound to the polypeptide, or fragment thereof, may be useful, but may be one exemplary assay or one assay among additional and more particular or specific assays to confirm the test compound is acting via a GPR84 polypeptide.

The order of taking these measurements is not believed to be critical to the practice of the present invention, which may be practiced in any order. For example, one may first perform a screening assay of a set of compounds for which no information is known respecting the compounds' binding affinity for the GPR84 polypeptide. Alternatively, one may screen a set of compounds identified as having binding affinity for a GPR84 domain, or a class of compounds identified as being an inhibitor of the polypeptide. However, for the present assay to be meaningful to the ultimate use of the drug candidate compounds, a measurement of the inhibition of GPR84-agonist stimulated chemotaxis by the test compound is considered essential. The means by which to measure, assess, or determine the effect on GPR84 activity, may be selected or determined by a skilled artisan. Validation studies including controls and measurements of binding affinity to the polypeptides or modulation of activity or expression of the polypeptides of the invention are nonetheless useful in identifying a compound useful in any therapeutic or diagnostic application.

In various embodiments binding of a test compound to GPR84 can be accomplished in any vessel suitable for containing the reactants. Examples of such vessels include microtiter plates and test tubes. A fusion protein can be provided which adds a domain that allows the GPR84 polypeptide to be bound to a matrix. For example, glutathione-S-transferase (GST) fusion proteins can be adsorbed onto glutathione sepharose beads (Sigma Chemical; St. Louis, Mo.) or glutathione derivatized microtiter plates, which are then combined with the test compound and the mixture incubated under conditions favorable for complex formation (e.g., at physiological conditions for concentration of salt and pH). Following incubation, the beads or microtiter plate wells are washed to remove any unbound components and complex formation is measured either directly or indirectly.

Particular drug candidate compounds are low molecular weight compounds. Low molecular weight compounds, for example with a molecular weight of 500 Dalton or less, are likely to have good absorption and permeation in biological systems and are consequently more likely to be successful drug candidates than compounds with a molecular weight above 500 Dalton (Lipinski et al., 2001)). Peptides comprise another particular class of drug candidate compounds. Peptides may be excellent drug candidates and there are multiple examples of commercially valuable peptides such as fertility hormones and platelet aggregation inhibitors. Natural compounds are another particular class of drug candidate compound. Such compounds are found in and extracted from natural sources, and which may thereafter be synthesized. The lipids are another particular class of drug candidate compound.

The provided methods might be performed using peptides in a phage display library or an antibody fragment libraries. For high-throughput purposes, libraries of compounds may be used such as antibody fragment libraries, peptide phage display libraries, peptide libraries (for example, LOPAP™, Sigma Aldrich), lipid libraries (BioMol), synthetic compound libraries (for example, LOPAC™, Sigma Aldrich, BioFocus) or natural compound libraries (Specs, TimTec, BioFocus).

Another particular class of drug candidate compounds is an antibody. The present invention also provides antibodies directed against a GPR84. These antibodies may be endogenously produced to bind to GPR84 or to one of its extracellular domains within the cell, or added to the tissue to bind to GPR84 polypeptide present outside the cell. These antibodies may be monoclonal antibodies or polyclonal antibodies. The present invention includes chimeric, single chain, and humanized antibodies, as well as Fab fragments and the products of a Fab expression library, and Fv fragments and the products of an Fv expression library. In another embodiment, the compound may be a nanobody, the smallest functional fragment of naturally occurring single-domain antibodies (Cortez-Retamozo et al. 2004). The antibodies include a domain antibody (dAb) fragment, which comprises a single variable domain; a camelid antibody; an isolated complementarity determining region (CDR); a Single Chain Fv Fragment; a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites; a linear antibody, which comprises a pair of tandem Fv segments (VH-CH1-VH-CH1) which, together with complementarity light chain polypeptides, form a pair of antigen binding regions; and other non-full length portions of heavy and/or light chains, or mutants, variants, or derivatives thereof, alone or in any combination.

In certain embodiments, polyclonal antibodies may be used in the practice of the invention. Methods of preparing polyclonal antibodies are well known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Antibodies may also be generated against the intact GPR84 protein or polypeptide, or against a fragment, derivatives including conjugates, or other epitope of the GPR84 protein or polypeptide, such as GPR84 embedded in a cellular membrane, or a library of antibody variable regions, such as a phage display library.

It may be useful to conjugate the immunizing agent to a protein known to be immunogenic in the mammal being immunized Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

In some embodiments, the antibodies may be monoclonal antibodies. Monoclonal antibodies may be prepared using methods known in the art. The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, for example, Mark and Padlan, (1994) "Chapter 4. Humanization of Monoclonal Antibodies", The Handbook of Experimental Pharmacology Vol. 113, Springer-Verlag, New York). Transgenic animals may be used to express humanized antibodies.

Human antibodies can also be produced using various techniques known in the art, including phage display libraries (Hoogenboom and Winter, (1991) J. Mol. Biol. 227:381-8; Marks et al. (1991). J. Mol. Biol. 222:581-97). The techniques of Cole et al. and Boerner et al. are also available for the preparation of human monoclonal antibodies (Cole, et al. (1985) Monoclonal Antibodies and Cancer Therapy, Alan R. Liss, p. 77; Boerner, et al (1991). J. Immunol, 147(1):86-95).

Techniques known in the art for the production of single chain antibodies can be adapted to produce single chain antibodies to the GPR84 polypeptide and protein of the present invention. The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Bispecific antibodies are monoclonal, particularly human or humanized, antibodies that have binding specificities for at least two different antigens and particularly for a cell-surface protein or receptor or receptor subunit. In the present case, one of the binding specificities is for one domain of GPR84, while the other one is for another domain of the same GPR84.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, (1983) Nature 305:537-9). Because of the random assortment of immunoglobulin heavy and light chains, these hybridomas (quadromas) produce a potential mixture of ten different antibody molecules, of which only one has the correct bispecific structure. Affinity chromatography steps usually accomplish the purification of the correct molecule. Similar procedures are disclosed in Trauneeker, et al. (1991) EMBO J. 10:3655-9.

As shown above and demonstrated by the examples the compounds which inhibit GPR84 and identified using methods as disclosed herein are useful in a therapeutic method, a pharmaceutical composition, and the manufacture of such composition, useful for the treatment of inflammatory conditions (for example inflammatory bowel diseases (IBD), rheumatoid arthritis, vasculitis, lung diseases (e.g. chronic obstructive pulmonary disease (COPD) and lung interstitial diseases (e.g. idiopathic pulmonary fibrosis (IPF)), neuroinflammatory conditions, infectious diseases, autoimmune diseases and/or diseases involving impairment of immune cell functions The invention is further illustrated in the following figures and examples.

EXAMPLES

As described above GPR84 appears to be an important component of inflammatory response regulation in particular influences the process of chemotaxis of the immune cells, more particularly neutrophils. The following assays, when used in combination with compound libraries are useful for the discovery of compounds useful in the treatment of inflammatory conditions.

Example 1 shows the results of GPR84 expression profiling in different cell types.

Example 2 demonstrates a method of identifying compounds which inhibit chemotaxis by inhibiting GPR84 activity.

Example 3 describes cell-based assay useful for determination of GPR84 activation The in vivo activity of the identified compounds of the invention was demonstrated in the following in vivo efficacy inflammation models:

Example 4 describes the in vivo testing of the selected compounds and demonstrates the in vivo effect of the compounds identified in the neutrophil migration assay Example 5 further demonstrates the effect of the identified compounds in COPD mouse model (mouse tobacco smoke model)

Example 1

GPR84 Expression Profiling

GPR84 Expression in Human Monocyte-Derived Macrophages and Dendritic Cells

The PBMC fraction was isolated out of buffy coats by density gradient techniques. Monocytes were isolated out of the PBMC fraction using positive selection with the MACS technology (CD14+ cell-selection).

For monocyte-derived macrophage differentiation, cells were seeded in 96 well plates and differentiation was initiated by culturing the cells for 5 days in presence of M-CSF (200 ng/mL). For monocyte-derived dendritic cells, cells were seeded in flasks and differentiation was initiated by culturing the cells for 5 days in presence of GM-CSF (90 ng/ml) and IL-4 (20 ng/mL). Once differentiated, cells were triggered with 100 ng/mL LPS. For monocyte-derived macrophages, LPS was added directly to the cells. For monocyte-derived dendritic cells, cells were harvested and seeded in U bottom plates at 20 000 cells/well. Then, LPS trigger was added to the cells. At the end of the treatment period, supernatants were discarded and cells were lysed in RLT buffer and stored at −80° C. until analysis GPR84 Expression in Human Neutrophils Blood freshly collected into heparinised tube is diluted with an equal volume of ice-cold DPBS. 20 mL of the diluted blood is gently mixed with 4 mL of ACD buffer (140 mM citric acid, 200 mM sodium citrate and 220 mM dextrose). Then, 12 mL of the dextran/NaCl (6% dextran/0.9% NaCl) solution was added to the mixture and the samples are inverted gently up to 20 times. The total volume is transferred to a new recipient and incubated at room temperature for 1 hour for complete separation of the two phases to occur. The yellowish supernatant is then transferred to a clean centrifugation tube and centrifuged for 12 minutes at 1300 rpm and 4° C. After centrifugation, the supernatant is discarded and the remaining cell pellet is rapidly re-suspended in 12 mL of ice-cold $H_2O$ for red blood cell lysis to occur. After 20 seconds, 4 mL of ice-cold 0.6 M KCl is added. Samples are mixed carefully and centrifuged for 6 minutes at 1300 rpm, 4° C. The supernatant is discarded and the red blood cell lysis procedure is repeated one more time. Subsequently, the cell pellet is resuspended in 4 mL of DPBS and layered over 5 mL of Lymphoprep™ in a 15 mL centrifuge tube. After centrifugation for 30 min at 1500 rpm, 4° C., the supernatant is removed and the cell pellet, containing the neutrophils, is resuspended in cell culture medium (RPMI+1% Glutamax+10 mM Hepes+10% HI FBS). 200 µL of cells at 5 million/mL are seeded in well (96 well plate) with 100 ng/mL LPS. After 4 or 24 hours of incubation at 37° C., 5% $CO_2$, 98% humidity, samples are transferred in microtubes and centrifuged. The pellet is resuspended in RLT buffer (Qiagen) and stored at −80° C. until analysis.

GPR84 Expression in T Cells

Spleens are harvested from female mice BALB/cJ and cell suspension of splenocytes is isolated by crushing spleens using a piston. After centrifugation (300×g for 10 minutes), CD4+CD62L+ T cell are isolated with the MACS technology according to the supplier's protocol (Miltenyi Biotec).

For Th17 polarization, 0.5 millions of CD4+CD62L+ T cells are incubated for 3 days at 37° C., 5% $CO_2$, 98% humidity in 24 well culture plates coated overnight with anti-mouse CD3ε (5 µg/mL) in presence of TGF-β1 (2.5 ng/mL), IL6 (20 ng/mL), anti-mouse IFN-γ (10 µg/mL), anti-mouse IL4 (10 µg/mL) and anti-mouse CD28 (1 µg/mL). At the end of incubation period, cells are collected, centrifuged and seeded in well (24 well plate) with 100 ng/mL LPS. After 4 or 24 hours of incubation at 37° C., 5%

CO$_2$, 98% humidity, samples are transferred in microtubes and centrifuged. Cell pellets are re-suspended in RLT buffer (Qiagen) and stocked at −80° C. until analysis.

For Th1 differentiation, 0.5 millions of CD4+CD62L+ T cells are incubated for 4 days at 37° C., 5% CO$_2$, 98% humidity in 24 well culture plates coated overnight with anti-mouse CD3ε (5 μg/mL), in presence of IL2 (10 ng/mL), IL12 (20 ng/mL), anti-mouse IL4 (20 μg/mL) and anti-mouse CD28 (6 μg/mL). At the end of incubation period, cells are collected, centrifuged and seeded in well (24 well plate) with IL2 (5 ng/mL) for 2 days of expansion at 37° C., 5% CO$_2$, 98% humidity. Then cells are collected, centrifuged and seeded in well (24 well plate) with 100 ng/mL LPS. After 4 or 24 hours of incubation at 37° C., 5% CO$_2$, 98% humidity, samples are transferred in microtubes and centrifuged. Cell pellets are resuspended in RLT buffer (Qiagen) and stocked at −80° C. until analysis.

For Th2 differentiation, 0.5 millions of CD4+CD62L+ T cells are incubated for 4 days at 37° C., 5% CO$_2$, 98% humidity in 24 well culture plates coated overnight with anti-mouse CD3ε (5 μg/mL) in presence of IL2 (10 ng/mL), IL4 (4 ng/mL), anti-mouse IFN-γ (10 μg/mL), anti-mouse IL12 (10 μg/mL) and anti-mouse CD28 (6 μg/mL). At the end of incubation period, cells are collected, centrifuged and seeded in well (24 well plate) with IL2 (5 ng/mL) for 2 days of expansion at 37° C., 5% CO$_2$, 98% humidity. Then cells are collected, centrifuged and seeded in well (24 well plate) with 100 ng/mLLPS. After 4 or 24 hours of incubation at 37° C., 5% CO$_2$, 98% humidity, samples are transferred in microtubes and centrifuged. Cell pellets are resuspended in RLT buffer (Qiagen) and stored at −80° C. until analysis.

GPR84 Expression in Rat Neutrophils 24 h after intraperitoneal injection of 20 mL of glycogen (0.1%, w/v), neutrophils are harvested by peritoneal lavage with 25 mL of PBS buffer. The exudates are centrifuged at 1150 rpm for 10 minutes at 4° C. (low brake). The supernatant is removed and the cells are suspended in 12 mL of the ice-cold distilled water in 50 mL Falcon tube. After 10-20 seconds 4 mL of 0.6 M KCl is added and mixed several times. Falcon tube is filled up to 50 mL with PBS. The tube is centrifuged at 1300 rpm for 6 minutes at 4° C. (high brake). The supernatant is removed, and the pellet is resuspended in 4 mL of PBS per Falcon tube. 4 mL of cell suspension is layered over 5 mL of Lymphoprep™ in a 15 mL Falcon tube and centrifuged at 1500 rpm for 30 minutes at 4° C. using a low brake. After being spun, the supernatant is taken off using mild aspiration with sterile tip and the cells are resuspended in cell culture medium (RPMI+1% Glutamax+10 mM Hepes+10% HI FBS. 200 μL of cells at 5 million/mL are seeded in well and 5 μL from RPMI or 100 ng/mL LPS are added. After 4 or 24 hours of incubation at 37° C., 5% CO$_2$, 98% humidity, samples are transferred in microtubes and centrifuged. The pellet were resuspended in RLT buffer and stored at −80° C. until analysis Total RNA Preparation & Analysis of GPR84 Expression by RT-QPCR Total RNA is extracted using the RNeasy Mini kit (Qiagen) following manufacturer's instructions. cDNA is prepared using cDNA Reverse Transcription Kit (Applied Biosystems) and Q-PCR is performed with SYBRGreen primers for GPR84 and GAPDH, as housekeeping gene. For data analysis, ΔCt values of GPR84 vs. the housekeeping gene GAPDH are calculated (ΔCt=Ct GPR84−Ct GAPDH).

TABLE 2

| Cell type | mRNA expression level under inflammatory condition* |
| --- | --- |
| Neutrophils | medium |
| Monocyte-derived macrophages | medium |
| Monocyte-derived dendritic cells | low |
| T cells (Th1, Th2, Th17) | medium |

*high (24 > Ct); medium (24 < Ct < 30); low (Ct > 30)

Example 2

Human Neutrophil Migration Inhibition Assay

We have established that GPR84 agonists (MCFA such as sodium decanoate, 3,3' di indolylmethane and Embelin) induce neutrophil chemotaxis and that GPR84 antagonists could block GPR84 agonist-stimulated chemotaxis but not IL8-stimulated chemotaxis, indicating that G Protein-Coupled Receptor 84 (GPR84) is an essential player in the process of neutrophil recruitment. The effect of agonists or antagonists for GPR84 can therefore be assayed in a neutrophil migration test. In the neutrophil migration assay, neutrophils, freshly isolated from buffy coats from human volunteers, are treated with a compound for 30 minutes. Subsequently, the neutrophils are transferred to the upper wells of a Corning HTS transwell 96 permeable support system, of which the lower wells are filled with a Embelin solution. After 1 h of incubation, migration of the neutrophils towards Embelin in the lower compartment can be quantified by measuring the ATP-content of the lower wells using the ATPlite luminescence ATP detection assay system (Perkin Elmer, Cat. N°.: 436110).

Isolation of Neutrophils from Human Buffy Coat

A human buffy coat is diluted with an equal volume of ice cold DPBS. 20 mL of the diluted buffy coat was gently mixed with 4 mL of ACD buffer (140 mM citric acid, 200 mM sodium citrate and 220 mM dextrose). Then, 12 mL of the 6% dextran/0.9% NaCl solution (15 g dextran T2000 and 2.25 g NaCl dissolved in 250 mL H$_2$O) is added to the mixture and the samples are inverted gently up to 20 times. The total volume is transferred to a new recipient and incubated at room temperature for 1 h for complete separation of the two phases to occur. The yellowish supernatant is then transferred to a clean centrifugation tube and centrifuged for 12 minutes at 1300 rpm and 4° C. After centrifugation, the supernatant is discarded and the remaining cell pellet is rapidly resuspended in 12 mL of ice-cold H$_2$O for red blood cell lysis to occur. After 20 seconds, 4 mL of ice-cold 0.6 M KCl is added. Samples are mixed carefully and centrifuged for 6 minutes at 1300 rpm, 4° C. The supernatant is discarded and the red blood cell lysis procedure is repeated one more time. Subsequently, the cell pellet is resuspended in 4 mL of DPBS and layered over 5 mL of Lymphoprep (Nycomed Pharma, Cat. N°.: 1114545) in a 15 mL centrifuge tube. After centrifugation for 12 min at 1300 rpm, 4° C., the supernatant is removed and the cell pellet, containing the neutrophils, is resuspended in 25 mL chemotaxis buffer (RPMI 1640 medium, supplemented with 10 mM HEPES; freshly made for each experiment).

Migration assay

A cell suspension of $8.9 \times 10^6$ cells per milliliter is prepared. 20 µL of compound solution in chemotaxis buffer is added to 180 µL cell suspension. The mixture is incubated at 37° C. for 30 minutes with intermediate resuspension of the cells after 15 minutes. Following this, 70 µL cell suspension is transferred to the upper compartment of a Corning HTS transwell 96 permeable support system with 5.0 µm pore size polycarbonate membrane (Corning, Cat. N°.: 3387). The receiver well of the transwell system is then filled with 200 µL chemotaxis buffer containing compound and chemotactic agent (Embelin). After incubation at 37° C. in 5% $CO_2$ for 1 h, the upper plate of the transwell system was removed and the cell suspension in the receiver plate is transferred to a 96-well V-bottom plate. 50 µL of DPBS is added to the receiver plate to prevent remaining cells from drying out. The V-bottom plate is centrifuged for 6 minutes at 1500 rpm. The supernatant is removed and the cells are resuspended in 50 µL DPBS. The cells are then transferred back to the receiver plate of the transwell system. After this, 100 µL ATPlite solution (Perkin Elmer, Cat. N°: 436110) is added to the cells. The plate is incubated for 10 minutes in the dark, while shaking. 170 µL of cell lysate is then transferred to a white 96-well plate and luminescence is measured. The detected luminescent signal is considered as linearly related to the number of cells having migrated from the upper well to the receiver well.

The same assay as described above is also performed using IL8 (25 ng/mL) as a chemotactic agent instead of Embelin.

The comparative results of chemotaxis inhibition at different concentrations of the test compounds are presented in Table 4. The structures of the tested compounds are listed in Table 3. Similar experiments using Capric acid as a chemotactic agent produce analogous results (data not shown)

TABLE 3

| Cpd # | Structure | Name |
|---|---|---|
| 1 | 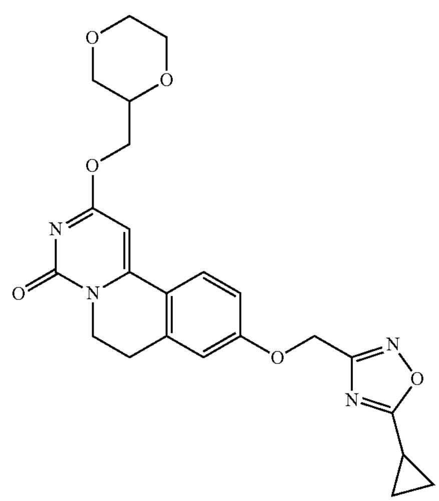 [SMILES: O=c1nc(OCC2COCCO2)cc2n1CCc1cc(OCc3noc(C4CC4)n3)ccc1-2] | 9-(5-Cyclopropyl-[1,2,4]oxadiazol-3-ylmethoxy)-2-([1,4]dioxan-2-ylmethoxy)-6,7-dihydro-pyrimido[6,1-a]isoquinolin-4-one |
| 2 | 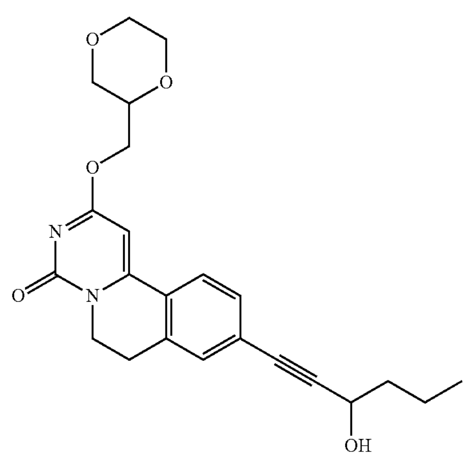 [SMILES: CCCC(O)C#Cc1ccc2c(c1)CCn1c-2cc(OCC2COCCO2)nc1=O] | 2-([1,4]Dioxan-2-ylmethoxy)-9-(3-hydroxy-hex-1-ynyl)-6,7-dihydro-pyrimido[6,1-a]isoquinolin-4-one |

TABLE 3-continued

| Cpd # | Structure | Name |
|---|---|---|
| 3 | 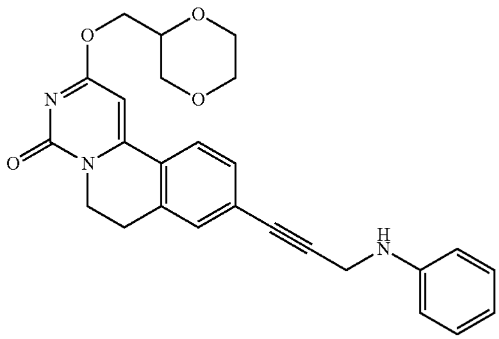 [SMILES: O=c1nc(OCC2COCCO2)cc2n1CCc1cc(C#CCNc3ccccc3)ccc1-2] | 2-([1,4]Dioxan-2-ylmethoxy)-9-(3-phenylamino-prop-1-ynyl)-6,7-dihydro-pyrimido[6,1-a]isoquinolin-4-one |
| 4 | 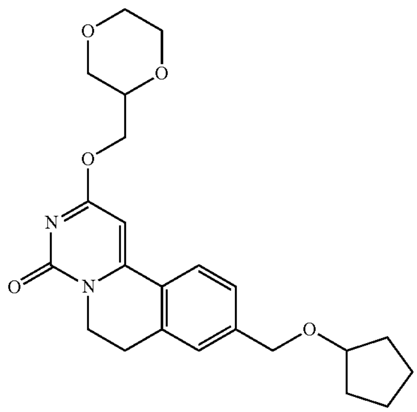 [SMILES: O=c1nc(OCC2COCCO2)cc2n1CCc1cc(COC3CCCC3)ccc1-2] | 9-Cyclopentyloxymethyl-2-([1,4]dioxan-2-ylmethoxy)-6,7-dihydro-pyrimido[6,1-a]isoquinolin-4-one |
| 5 | Chiral | 2-((S)-1-[1,4]Dioxan-2-ylmethoxy)-9-(3-methyl-but-1-ynyl)-6,7-dihydro-pyrimido[6,1-a]isoquinolin-4-one |
| 6 | 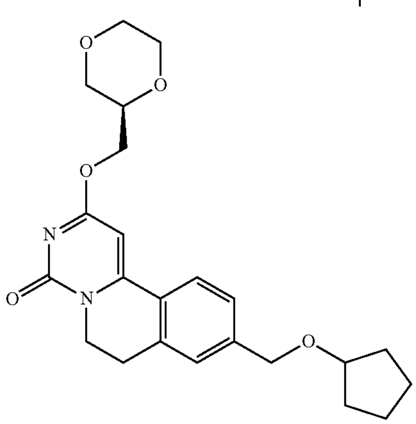 | 9-Cyclopentyloxymethyl-2-((R)-1-[1,4]dioxan-2-ylmethoxy)-6,7-dihydro-pyrimido[6,1-a]isoquinolin-4-one |

TABLE 3-continued

| Cpd # | Structure | Name |
|---|---|---|
| 7 | 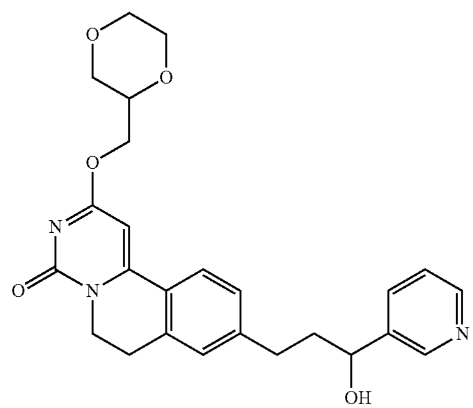 [SMILES: O=c1nc(OCC2COCCO2)cc2n1CCc1cc(CCC(O)c3cccnc3)ccc1-2] | 2-([1,4]Dioxan-2-ylmethoxy)-9-(3-hydroxy-3-pyridin-3-yl-propyl)-6,7-dihydro-pyrimido[6,1-a]isoquinolin-4-one |
| 8 | 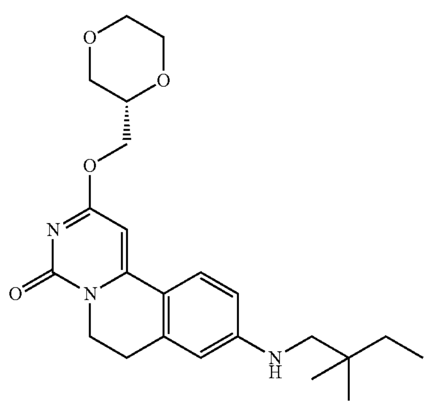 [SMILES: CCC(C)(C)CNc1ccc2c(c1)CCn1c-2cc(OC[C@@H]2COCCO2)nc1=O] | 9-(2,2-Dimethyl-butylamino)-2-((S)-1-[1,4]dioxan-2-ylmethoxy)-6,7-dihydro-pyrimido[6,1-a]isoquinolin-4-one |
| 9 | 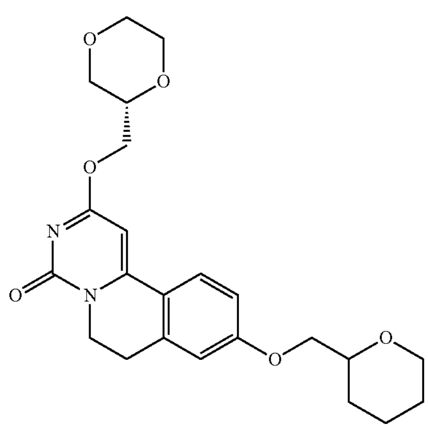 [SMILES: O=c1nc(OC[C@@H]2COCCO2)cc2n1CCc1cc(OCC3CCCCO3)ccc1-2] | 2-((S)-1-[1,4]Dioxan-2-ylmethoxy)-9-(tetrahydro-pyran-2-ylmethoxy)-6,7-dihydro-pyrimido[6,1-a]isoquinolin-4-one |
| 10 | 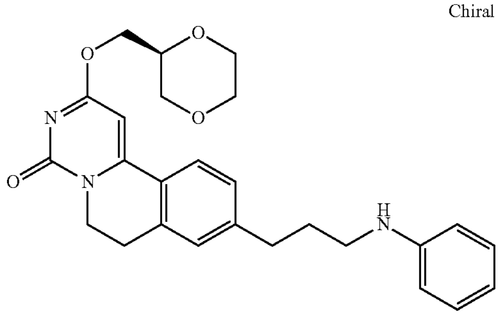 [SMILES: O=c1nc(OC[C@@H]2COCCO2)cc2n1CCc1cc(CCCNc3ccccc3)ccc1-2] | Chiral 2-((S)-1-[1,4]Dioxan-2-ylmethoxy)-9-(3-phenylamino-propyl)-6,7-dihydro-pyrimido[6,1-a]isoquinolin-4-one |

TABLE 3-continued

| Cpd # | Structure | Name |
|---|---|---|
| 11 | 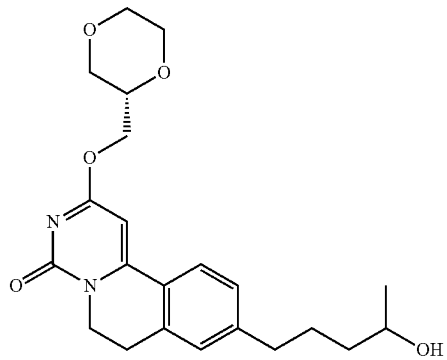 [SMILES: CC(O)CCCc1ccc2c(c1)CCn1c-2cc(OC[C@@H]2COCCO2)nc1=O] | 2-((S)-1-[1,4]Dioxan-2-ylmethoxy)-9-(4-hydroxy-pentyl)-6,7-dihydro-pyrimido[6,1-a]isoquinolin-4-one |
| 12 | 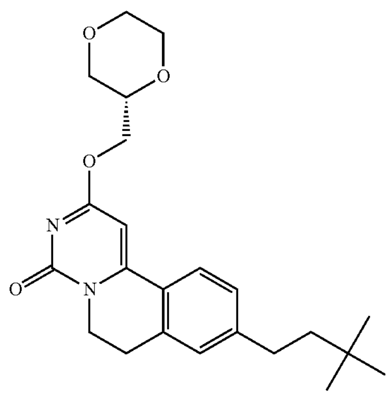 [SMILES: CC(C)(C)CCc1ccc2c(c1)CCn1c-2cc(OC[C@@H]2COCCO2)nc1=O] | 9-(2,2-Dimethyl-propoxy)-2-((S)-1-[1,4]dioxan-2-ylmethoxy)-6,7-dihydro-pyrimido[6,1-a]isoquinolin-4-one |

TABLE 4

Results of the inhibition of IL8- and Embelin-induced chemotaxis using different test compounds

| | Embelin-induced | Percentage of chemotaxis inhibition (PIN) | | | | | |
|---|---|---|---|---|---|---|---|
| | neutrophil | 25 ng/mL IL8 | | | 5 µM Embelin | | |
| Cpd# | chemotaxis IC50, nM | PIN @ 0.1 µM | PIN @ 1 µM | PIN @ 10 µM | PIN @ 0.1 µM | PIN @ 1 µM | PIN @ 10 µM |
| 1 | 10.4 | 1 | −11 | 17 | 69 | 86 | 89 |
| 2 | 2.74 | 13 | −6 | 20 | 86 | 94 | 90 |
| 3 | 6.34 | 2 | 1 | −13 | 38 | 81 | 72 |
| 4 | 6.5 | 3 | 3 | 19 | 82 | 89 | 82 |
| 5 | 62.2 | 30 | 29 | 48 | 73 | 97 | 96 |
| 6 | 12 | 20 | 15 | 35 | 79 | 94 | 89 |
| 7 | 83.4 | 18 | 22 | 13 | 54 | 90 | 81 |
| 8 | 41.4 | 9 | 15 | 55 | 52 | 95 | 103 |
| 9 | 40.8 | 25 | 28 | 24 | 64 | 94 | 88 |
| 10 | 9.3 | 13 | 7 | 24 | 71 | 87 | 80 |
| 11 | 3.9 | 7 | 0 | 12 | 66 | 90 | 86 |
| 12 | 4.2 | 15 | 18 | 78 | 58 | 91 | 108 |

Example 3

Rat Neutrophil Migration Assay

The effect of agonists or antagonists for GPR84 can be assayed in a neutrophil migration test using neutrophils from rats. In the rat neutrophil migration assay, neutrophils, freshly isolated from rat after intraperitoneal injection of glycogen (0.1%, w/v), are treated with a compound for 30 minutes. Subsequently, the neutrophils are transferred to the upper wells of a Corning HTS transwell 96 permeable support system, of which the lower wells are filled with a embelin solution at $EC_{80}$ (concentration which gives 80% of the activity of the GPR84). After 1 h of incubation, migration of the neutrophils towards embelin in the lower compartment can be quantified by measuring the ATP-content of the lower wells using the Cell Titer Glow Substrate assay system (Promega, Cat. N°.: G755B).

Isolation of Neutrophils from Rats 24 h after intraperitoneal injection of glycogen (0.1%, w/v), cells are harvested by peritoneal lavage with 25 mL HBSS then centrifuged for 12 minutes at 1300 rpm and 4° C. After centrifugation, the supernatant is discarded and the remaining cell pellet is rapidly resuspended in 12 mL of ice-cold $H_2O$ for red blood cell lysis to occur. After 20 seconds, 4 mL of ice-cold 0.6 M KCl is added. Samples are mixed carefully and centrifuged for 6 minutes at 1300 rpm, 4° C. The supernatant is discarded and the cell pellet is resuspended in 4 mL of DPBS and layered over 5 mL of Lymphoprep (Axis Shield, Cat. N°: 1114544) in a 15 mL centrifuge tube. After centrifugation for 30 min at 1500 rpm, 4° C., the supernatant is removed and the cell pellet, containing the neutrophils, is resuspended in 5 mL chemotaxis buffer (RPMI 1640 medium, supplemented with 10 mM HEPES; freshly made for each experiment).

Neutrophil Migration Assay

A cell suspension of $8.9 \times 10^6$ cells per milliliter is prepared. 10 µL of compound solution in chemotaxis buffer is added to 90 µL of the cell suspension. The mixture is incubated at 37° C. for 30 minutes with intermediate resuspension of the cells after 15 minutes. Following this, 75 μL cell suspension is transferred to the upper compartment of a Corning HTS transwell 96 permeable support system with 5.0 μm pore size polycarbonate membrane (Corning, Cat. N°.: 3387). The receiver well of the transwell system is then filled with 200 μL chemotaxis buffer containing compound and chemotactic agent (embelin). After incubation at 37° C. in 5% $CO_2$ for 1 h, the upper plate of the transwell system is removed and 70 μL Cell Titer Glow Substrate (Promega, Cat. N°.: G755B) are added in the receiver plate. The receiver plate is incubated for 10 minutes in the dark, while shaking. 180 μL of cell lysate is then transferred to a white 96-well plate and luminescence is measured. The detected luminescent signal is considered as linearly related to the number of cells having migrated from the upper well to the receiver well.

Example 4

Functional GPR84 Activation Assay: GTP-γS Binding Assay

The following assay can be used for determination of GPR84 activation. The [$^{35}$S]GTPγS binding assay measures the level of G protein activation following agonist occupation of a GPCR, by determining the binding of the non-hydrolysable analog [$^{35}$S]GTPγS to Gα subunits.

The assay is performed in a 96 well plate where the following reagents were added. First 50 μL compound is added into the assay plate, followed by addition of 20 μL 3,3' di indolylmethane at $EC_{80}$ concentration (concentration which give 80% of the activity of the GPR84). In a last step, 30 μL of a mixture consisting of membranes-GTPγS-SpA beads is added [mixture consists of 20 μg/well membranes derived from stable cell line over expressing GPR84 (membranes are pre-incubated with 0.1 μM GDP for 15 min at 4° C.), 0.1 nM [$^{35}$S]GTPγS (Perkin Elmer, NEG030) and 0.5 mg/well PVT-WGA SpA beads (Perkin Elmer, RPNQ0001)]. All components are diluted in assay buffer containing 20 mM Hepes pH 7.4; 5 mM $MgCl_2$; 250 mM NaCl; 0.05% BSA; 75 ug/mL saponin. Reactions are incubated for 90 min at room temperature followed by centrifugation at 2000 rpm for 15 min. Plates are read on a Topcount reader (Perkin Elmer) immediately after centrifugation (readout time, 1 min/well). The results of the $EC_{50}$ measurements for the compounds identified in the neutrophil migration assay from the Example 2 are listed in the Table 5 below.

TABLE 5

The $EC_{50}$ values measured in the GPR84 GTP-γS binding assay

| Cpd# | GTPgS binding $EC_{50}$, nM |
|---|---|
| 1 | 36 |
| 2 | 40 |
| 3 | 25 |
| 4 | 13 |
| 5 | 77 |
| 6 | 25 |
| 7 | 41 |
| 8 | 69 |
| 9 | 75 |
| 10 | 8 |
| 11 | 58 |
| 12 | 93 |

Example 5

In Vivo IBD Model

The compounds identified using the assay method described in Example 2, or others herein, can be further validated in vivo using known disease models. The mouse chronic DSS-induced inflammatory bowel disease model (IBD) is a well validated disease model for inflammatory bowel disease (Wirtz S. et al., 2007 Nature Protocols 2, 541-546; Sina C. et al., 2009 J. Immunol 183 7514-7522).

To induce a chronic colitis, female BALB/c mice are fed with 4% dextran sodium sulfate (DSS) dissolved in drinking water for 4 days, followed by 3 days of regular drinking water. This cycle is repeated three times. This protocol allows inducing a strong colitis while avoiding high mortality rates. Animals are divided into several groups:
    intact (water; vehicle alone, n=10),
    diseased (DSS; vehicle alone, n=10),
    sulfazalazine used as reference (DSS; sulfazalazine, p.o., n=10) and
    the tested compound (DSS; test cpd, p.o., n=10).

Clinical parameters are measured every other day. The disease activity index (DAI) is a composite measure combining of the individual scores for weight loss, stool consistency and rectal bleeding. Mice are sacrificed at day 20 of the experiment according to the protocol introduced by Sina et al. (2009). At sacrifice time, the complete colon is removed and rinsed with sterile PBS. Segments of the distal colon are dissected for histological analysis, gene expression and protein level measurement.

Some of the compounds identified as active in the chemotaxis assay were tested in IBD model. Groups treated with sulfazalazine and/or a test compound exhibited protective effect against chronic inflammatory bowel disease (data not shown).

Example 6

In Vivo Mouse Smoke Model Testing

Daily exposures C57BL/6J mouse strain to tobacco smoke (TS) for 4 consecutive days resulted in pulmonary inflammation, and was indicated by an increase in the total number of cells recovered in the bronchoalveolar lavage (BAL), when compared with a similarly treated air-exposed group, 24 h after the final exposure.

To investigate test compounds, animals are divided into several groups: intact (no treatment, n=5), diseased (TS; vehicle alone, n=10), Roflumilast as reference (TS; Roflumilast n=10), and the test compound (TS; test cpd, p.o., n=10). A test compound or vehicle are administered orally (p.o.) 1 h prior to and 6 h after each of 4 daily exposures to TS. At the end of 4 days, the numbers of macrophages, epithelial cells, neutrophils and lymphocytes are counted in the BAL. BAL was further analyzed for gene expression and protein level. Lung tissue is dissected for histological analysis, gene expression and protein level measurement.

Some of the compounds identified in the chemotaxis assay described in Example 2 have been validated using this model. The total number of cells was significantly decreased, but especially the number of neutrophils present in the BAL. In some cases the percentage inhibition was measured around 60% for the neutrophil counts, similaraly to the reference Roflumilast (data not shown).

REFERENCES

Baggiolini (1998) Nature 392 (6676) 565-568.
Berry et al. (2010) Nature, 466, 973-979

Bouchard et al. (2007) Glia, 55:790-800
Brand et al (2007) Nature Protocols 2, 1269-1275
Bundgard (1985) Design of Prodrugs, pp. 7-9, 21-24, Elsevier, Amsterdam 1985
Chung et al (2001) Trends Biochem. Sci. 26 (9), 557-566.
Du Bois (2010) Nat Rev, Drug Discovery 9, 129
Foxman et al (1997) J. Cell Biol. 139 (5) 1349-1360.
Foxman et al (1999) J. Cell Biol. 147 (3) 577-588.
Khachigian et al (2006) Nature Protocols 1, 2512-2516
Kubes (2002) Semin. Immunol 14 (2) 65-72.
Lin et al (2007) Br J Pharmacol 1, 829-831
Salvemini et al (2001) Arthritis Rheum 44, 2909-2921
Sina C. et al (2009) J. Immunol 183 7514-7522
Takeda et al (2003) Life Sciences, 74, 367-377
Venkataraman et al (2005) Immunology Letters, 101, 144-153
Wang et al (2006) The Journal of Biological Chemistry, 281, 45, 3457-3464
Wells et al (2005) *Methods Mol. Biol.* 294, 31-34.
Wirtz S. et al (2007) Nature Protocols 2, 541-546
Wittenberger et al (2001) J Mol Biol, 307, 799-813
Woolhouse et al (2002) Thorax 57 (8) 709-714.
WO2007/027661
Young et al (2007) Bioorganic & Medicinal Chemistry 15, 2667-2679
Yousefi S et al (2001) J Leukoc Biol, 69, 1045-52
Zicha et al (1991) J Cell Sci 99, 769-775
Zicha D et al (1997) *Methods Mol. Biol.* 75, 449-457.
Zigmond (1988). "Methods Enzymol 162: 65-72

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

We claim:

1. A method for identifying a compound that inhibits G protein coupled receptor 84 (GPR84) agonist-stimulated chemotaxis, said method comprising:
   a. exposing a population of cells expressing a GPR84 polypeptide comprising the amino acid sequence of SEQ ID NO: 1 to a test compound in the presence of a GPR84 agonist;
   b. measuring GPR84 agonist-stimulated chemotaxis of said cells, wherein chemotaxis is measured by determining the number of migrated cells; and
   c. comparing GPR84 agonist-stimulated chemotaxis of said cells in the presence of said test compound with a control in which GPR84 agonist-stimulated chemotaxis is not inhibited and identifying the compound as an inhibitor of GPR84 agonist-stimulated chemotaxis when chemotaxis in the presence of the compound is decreased compared to control.

2. The method of claim 1, further comprising:
   d. exposing a population of cells expressing a GPR84 polypeptide comprising the amino acid sequence of SEQ ID NO: 1 to a test compound in the presence of a chemotactic agent that is not a GPR84 agonist;
   e. measuring non-GPR84 agonist-stimulated chemotaxis of said cells, wherein chemotaxis is measured by determining the number of migrated cells; and
   f. comparing non-GPR84 agonist-stimulated chemotaxis of said cells in the presence of said test compound with a control in which non-GPR84 agonist-stimulated chemotaxis is not inhibited and identifying the compound as a specific inhibitor of GPR84 agonist-stimulated chemotaxis when non-GPR84 agonist-stimulated chemotaxis in the presence of the compound is not decreased compared to control.

3. The method of claim 2, wherein said chemotactic agent is selected from the group consisting of Interleukin-8 (IL8; human), chemokine (C—X—C motif) ligand 1 (KC/CXCL1; rat), N-formylmethionyl-leucyl-phenylalanine (fMLP), leukotriene B4 or complement 5a.

4. The method of claim 3, wherein said test compound identified as inhibiting GPR84 agonist-stimulated chemotaxis is contacted with cells stimulated with IL8- or LTB4 and identified as a specific inhibitor GPR84 agonist-stimulated chemotaxis if said compound does not inhibit IL8- or LTB4-stimulated chemotaxis in said cells.

5. The method of claim 1, further comprising comparing GPR84 agonist-stimulated chemotaxis of said cells in the presence of said test compound with a control wherein said control comprises a population of cells expressing a GPR84 polypeptide comprising the amino acid sequence of SEQ ID NO: 1 exposed to a known antagonist of the GPR84 polypeptide in the presence of a GPR84 agonist.

6. The method of claim 1 wherein said population of cells are immune cells selected from the group consisting of dendritic cells, macrophages, and neutrophils.

7. The method according to claim 6, wherein said population of cells are neutrophils.

8. The method of claim 1 wherein said GPR84 agonist is selected from the group comprising capric acid, undecanoic acid, lauric acid, 2,5-Dihydroxy-3-undecyl-2,5-cyclohexadiene-1,4-dione (Embelin), icosa-5,8,11,14-tetraynoic acid, 5S,6R-Dihydroxy-icosa-7,9,11,14-tetraynoic acid, diindorylmethane and indol-3-carbinol.

9. The method of claim 8, wherein said GPR84 agonist is 2,5-Dihydroxy-3-undecyl-2,5-cyclohexadiene-1,4-dione (Embelin) or capric acid.

10. The method of claim 1 wherein said method for measuring the number of cells migrated is measurement of ATP level change in a chemotaxis measurement system comprising two separate compartments.

11. The method of claim 1, wherein the method for determining the number of migrated cells is by using Zigmond chambers to perform time-lapse video microscopy.

12. The method of claim 1, wherein the method for determining the number of migrated cells is with a Dunn chemotaxis chamber to obtain a microscopic readout.

13. The method of claim 1, wherein the number of migrated cells is determined by a cell count of migrated cells.

14. The method of claim 1, further comprising:
   d. selecting a compound with a desired level of binding affinity to said polypeptide by:
      i. contacting said test compound identified as inhibiting GPR84 agonist-stimulated chemotaxis with a GPR84 polypeptide comprising the amino acid sequence of SEQ ID NO: 1 and/or fragments thereof comprising an amino acid sequence selected from the group consisting of SEQ ID NO 2, 6, 10, and 14; and
      ii. measuring the binding affinity of said test compound to said GPR84 polypeptide or fragment thereof; and
      iii. selecting a compound with a desired level of binding affinity to said polypeptide.

15. The method according to claim 14, wherein compounds are selected with a binding affinity of at least 10 µM.

* * * * *